US008148609B2

(12) United States Patent
Koprowski et al.

(10) Patent No.: US 8,148,609 B2
(45) Date of Patent: Apr. 3, 2012

(54) USES FOR YERBA SANTA

(76) Inventors: Hilary Koprowski, Wynnewood, PA (US); Natalia Pogrebnyak, Highland Park, NJ (US); Maxim Golovkin, Philadelphia, PA (US)

( * ) Notice: Subject to any disclaimer, the term of this patent is extended or adjusted under 35 U.S.C. 154(b) by 343 days.

(21) Appl. No.: 12/487,942

(22) Filed: Jun. 19, 2009

(65) Prior Publication Data

US 2010/0009913 A1 Jan. 14, 2010

Related U.S. Application Data

(60) Provisional application No. 61/074,376, filed on Jun. 20, 2008.

(51) Int. Cl.
*C12N 15/82* (2006.01)
*A01H 5/00* (2006.01)
*A61K 38/00* (2006.01)
*A61K 36/00* (2006.01)

(52) U.S. Cl. ........ 800/294; 800/278; 800/288; 800/295; 800/298; 435/468; 435/419; 424/184.1; 424/439

(58) Field of Classification Search ........................ None
See application file for complete search history.

(56) References Cited

OTHER PUBLICATIONS

Cao et al. Transformation of recalcitrant turfgrass cultivars through improvement of tissue culture and selection regime. (2006) Plant Cell, Tissue and Organ Culture; vol. 85; pp. 307-316.*
Curtis et al. A stable transformation system for the ornamental plant, *Datura meteloides* D. C. (1999) Plant Cell Reports; vol. 18; pp. 554-560.*
Liu, et al., (1992) J Nat Prod 55:357-363.
Heizer, et al., (1980) The Natural World of the California Indians, University of California Press, Berkeley & Los Angeles, California, p. 132.
Hansson, et al., (2000) Biotechnol Appl Biochem 32:95-107.
Daniell, et al., (2001) Trends Plant Sci 6:219-226.
Ma, et al., (2003) Nat Rev Genet 4:794-805.
Kaprowski, H. (2005) Vaccine 23:1757-1763.
Pogrebnyak, et al., (2005) Proc Natl Acad Sci USA 102:9062-9067.
Golovkin, et al., (2007) Proc Natl Acad Sci USA 104:6864-6869.
Goldstein, et al. (2004) QJ Med 97:705-716.
O'Keefe B. et al., (2009) Proc Natl Acad Sci USA 106:6099-6104.
Giddings, et al., (2005) Nat Biotechnol 18:1151-1155.
Pogrebnyak, et al., (2006) Plant Sci. 171:677-685.
Mori, et al., (2005) "Isolation and characterization of griffithsin, a novel HIV-inactivating protein, from the red alga *Griffithsia* sp" J. Biol. Chem. 280(10):9345-53.
Fischer, et al., (1999) "Affinity-purification of a TMV-specific recombinant full-size antibody from a transgenic tobacco suspension culture" J. of Immunological Methods 226:1-10.
Hoofer, et al. (2001) "The Central Nervous System Inflammatory Response to Neurotropic Virus Infection Is Peroxynitrite Dependent" J. of Immunology 167:3470-3477.
Murashige, et al., (1962) "A Revised Medium for Rapid Growth and Bio Assays with Tobacco Tissue Cultures" Physiologia Plantarum, vol. 15, 473-497.

* cited by examiner

*Primary Examiner* — Cathy Kingdon Worley
(74) *Attorney, Agent, or Firm* — Ballard Spahr LLP

(57) ABSTRACT

Methods of in vitro propagation of plants of the genus *Eriodictyon* are described, including, in particular embodiments, plants of the species *E. californicum, E. trichocalyx* and *E. sessilifolium*. Methods of producing transgenic plants of the genus *Eriodictyon* are also described, along with methods of producing recombinant proteins in such plants. Compositions and methods for administering recombinant proteins produced in these plants are also described.

36 Claims, 7 Drawing Sheets

A B C D

A

B

USES FOR YERBA SANTA

CROSS-REFERENCE TO RELATED APPLICATIONS

This application claims priority from U.S. Provisional Application No. 61/074,376 filed on Jun. 20, 2008, the disclosure of which is herein incorporated by reference.

STATEMENT REGARDING FEDERALLY SPONSORED RESEARCH OR DEVELOPMENT

This invention was made with United States government support awarded by the United States Department of Agriculture, Grant Number SCA 58-1275-4-303. The United States has certain rights in this invention.

BACKGROUND OF THE INVENTION

The medicinal plant Yerba Santa, member of the Waterleaf Family, genus *Eriodictyon*, has a long tradition of use. Yerba Santa (including *Eriodictyon californicum, Eriodictyon trichocalyx* and other related species) has been used in treating respiratory conditions, including colds, cough, asthma and bronchitis. This herb has also been found effective for a number of other symptoms including gastrointestinal disorders, fatigue, rheumatism, and allergies. Biochemical analyses have confirmed Yerba Santa to have flavonoids that show promise as anti-carcinogens (Liu Y L, Ho D K, Cassady J M, Cook V M, Baird W M (1992) *J Nat Prod* 55:357-363).

For medical purposes, Yerba Santa has been used as either a dry herb or an extract. (Heizer R F, Elsasser A B (1980) The natural world of the California Indians, University of California Press, Berkeley & Los Angeles, Calif. 271 pp.). Many herbal stores carry different products containing Yerba Santa such as, for example, leaf powder, extracts, leaf tea, and cream. The fluid Yerba Santa extracts have been used in food, beverages, pharmaceuticals and cosmetics.

Yerba Santa is a perennial evergreen shrub (1-2 meters) that grows in dry, hilly areas of California and Northern Mexico. During dry months, the leaves become hard and resinous in order to hold and conserve water. When applied to mucosal surfaces, the herb preparation holds the aqueous component in contact with cells, reestablishing mucopolysaccharides. It is hypothesized that this property may facilitate the adherence to the mucosa of compositions such as, for example, pharmaceutical agents.

In recent years, there has been an increased interest in mass multiplication of this unique plant. In vitro culture techniques have been used successfully for large scale production of many medicinally important plant species. However, methods for in vitro propagation and tissue culture techniques for Yerba Santa have not previously been described.

Plant biotechnology has provided successful tissue culture and transformation technologies for a variety of plants. However, the use of biotechnological tools in medicinal plant science has been very limited as compared to other crops. Nevertheless, in recent years such techniques have been developed for number of important medicinal plants such as *Ginkgo biloba, Digitalis lanata, Artenisia annua, Papaver somniferum, Camptotheca acuminate, Ophiorrhiza prostrate*, and *Mentha piperita*. Although Yerba Santa is a very important medicinal plant, there have been no techniques described for in vitro propagation, cell culture cultivation, regeneration and transformation of this perennial shrub.

Modern plant biotechnology has opened new avenues for producing recombinant molecules, including, but not limited to, vaccines (Hansson M, Nygren P A & Stahl S (2000) *Biotechnol Appl Biochem* 32:95-107; Daniell H, Streatfield S J & Wycoff K (2001) *Trends Plant Sci* 6:219-226; Ma J K C, Drake P M W & Christou P (2003) *Nat Rev Genet* 4:794-805; Koprowski H (2005) *Vaccine* 23:1757-1763; Pogrebnyak N., Golovkin M., Andrianov V., Spitsin S., Smirnov Y., Egolf R., Koprowski H (2005) *Proc Natl Acad Sci USA* 102: 9062-9067; and Golovkin M., Spitsin S., Andrianov V., Smirnov Y., Xiao Y., Pogrebnyak N., Markley K., Brodzik R., Gleba Y., Isaacs S N, Koprowski H. *Proc Natl Acad Sci USA* (2007), 104: 6864-6869; Goldstein D A, Thomas J A (2004) *QJ Med* 97:705-716) or microbicides (O'Keefe B. et al. *Proc Natl Acad Sci USA* (2009), 106: 6099-6104). This approach has become an attractive alternative to other technologies since it is associated with low production cost, overall safety, and scalability potential. A potential benefit of using plants for vaccine production is the possibility of applying preparations directly to bodily surfaces such as, for example, mucosal surfaces (Goldstein D A, Thomas J A (2004) *QJ Med* 97:705-716; Giddings G, Allison G, Brooks D, Carter A (2005) *Nat Biotechnol* 18:1151-1155; Pogrebnyak N. Markley K., Smirnov Y., Brodzik R., Bandurska K., Koprowski H., Golovkin M (2006) *Plant Sci.* 171: 677-685); Golovkin M., Spitsin S., Andrianov V., Smirnov Y., Xiao Y., Pogrebnyak N., Markley K., Brodzik R., Gleba Y., Isaacs S N, Koprowski H. *Proc Natl Acad Sci USA* (2007), 104: 6864-6869; O'Keefe B. et al. *Proc Natl Acad Sci USA* (2009), 106: 6099-6104).

BRIEF SUMMARY OF INVENTION

The invention relates to a transgenic plant of the genus *Eriodictyon*, in particular plants of the species *E. californicum, E. trichocalyx* or *E. sessilifolium*. In one aspect, the transgenic plant expresses a recombinant protein selected from the group consisting of antigens, microbicides, antibodies, hormones, enzymes, blood components, interferons, and anticoagulants. In a particular embodiment, the antigen is a viral protein such as an avian influenza HA1 antigen. In another embodiment, the microbicide is an antiretroviral such as griffithsin.

In another embodiment, the present invention relates to a method for transforming a plant tissue, particularly plant tissue from a plant species of the genus *Eriodictyon* including the steps of: inoculating a transformable plant tissue with an *Agrobacterium* suspension, the *Agrobacterium* containing at least one genetic component encoding a desired protein capable of being transferred to the transformable plant tissue and of directing the expression of the desired protein in the plant tissue; co-cultivating the plant tissue with the *Agrobacterium*; transferring the plant tissue to recovery media containing an antibiotic for eliminating the *Agrobacterium*; and selecting transformed plant tissue.

The invention also relates to a method for producing a recombinant protein in a transgenic plant of the genus *Eriodictyon* including the steps of: providing a transgenic plant that has been regenerated from a transformed plant cell or tissue of the genus *Eriodictyon* and that expresses a recombinant protein; and recovering the protein expressed in the transgenic plant.

One embodiment of the present invention relates to a method of delivering a recombinant protein to a subject including providing harvested material from a transgenic plant of the genus *Eriodictyon* that expresses a recombinant protein; and administering the harvested material to the subject in an amount necessary to deliver an effective amount of the recombinant protein. In a particular aspect, the recombinant protein is an antigen and the harvested material is administered in an amount sufficient to induce an immune response in the subject. In another aspect, the recombinant protein is a microbicide and the harvested material is administered in an amount sufficient to provide a prophylactic effect.

In another embodiment, the invention relates to a method of propagating in vitro a plant of the genus *Eriodictyon*, the method including the steps of: excising a stem segment of the plant; and incubating the segment in a growth medium comprising a cytokinin; whereby the segment produces a shoot. In another aspect, the method further includes excising the shoot; and incubating the excised shoot in medium comprising an auxin, whereby the shoot produces a root.

In another embodiment, the method of propagating in vitro a plant of the genus *Eriodictyon* further includes incubating the shoot for at least three weeks, whereby the shoot produces a leaf; cutting a segment from the leaf; placing the segment in a culture medium comprising one or more of benzylaminopurine, naphthaleneacetic acid or 2,4-dichlorophenoxyacetic acid; and incubating the segment in the dark, whereby the segment develops callus tissue.

In another aspect, the invention relates to a method of producing a cell suspension culture of a plant of the genus *Eriodictyon* including the steps of: excising a portion of the callus tissue produced according to certain aspects of the invention; placing the callus tissue in a liquid medium comprising 2,4-dichlorophenoxyacetic acid to form a cell suspension; and incubating the cell suspension in the dark while agitating the medium.

DETAILED DESCRIPTION OF THE INVENTION

Figure 1:
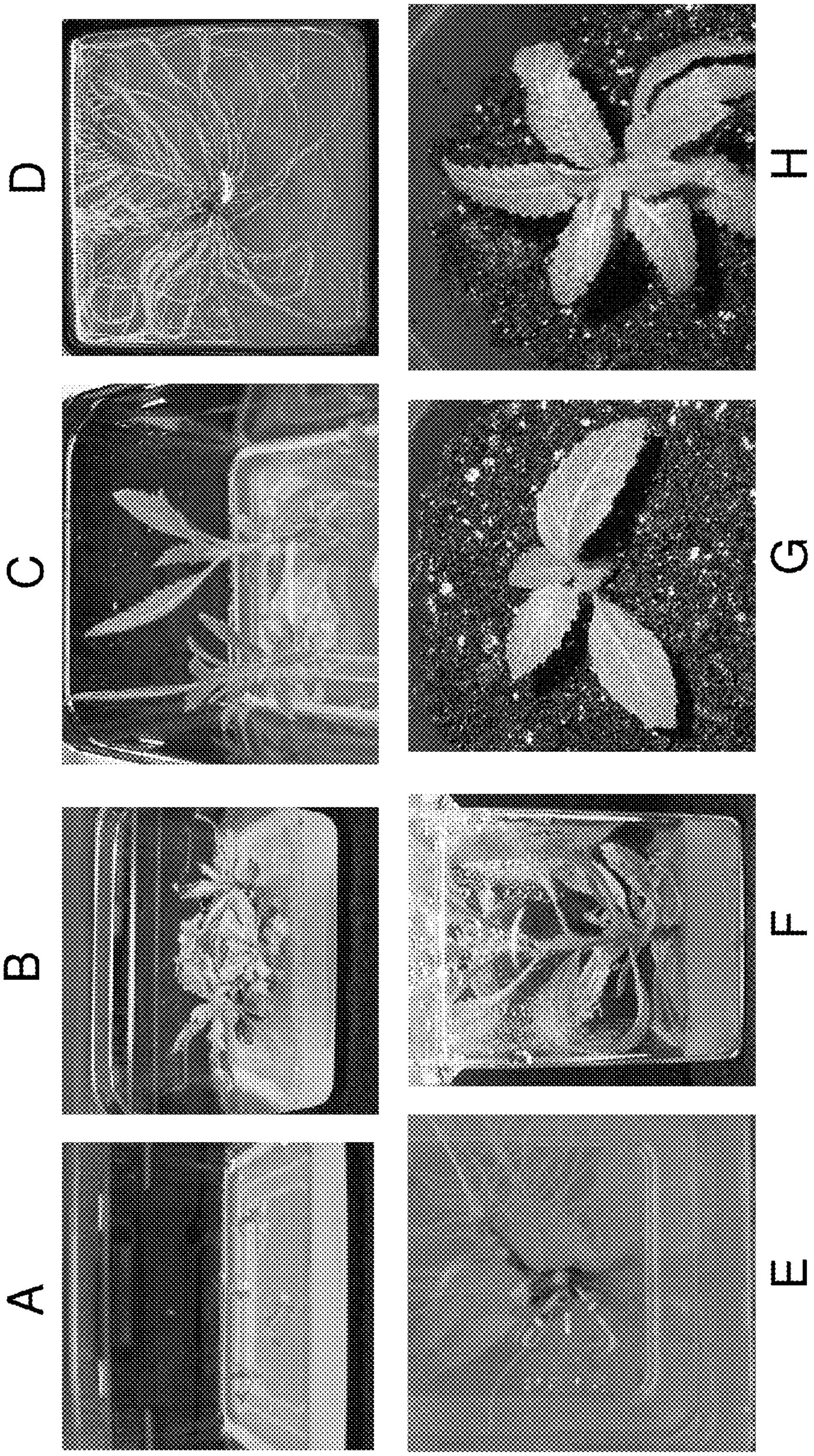
FIG. 1 illustrates in vitro propagation of Yerba Santa. (A) Yerba Santa *E. trichocalyx* stem segments, 3 days on MS medium with 1 mg/l zeatin (B) *E. trichocalyx* stem segments produced multiple shoots after 5 weeks on MS medium with 1 mg/l zeatin. (C) Root formation in *E. sessilifolium* after 10 days on MS medium. (D) Root induction in *E. trichocalyx* on MS medium with 1 mg/l IBA, view of bottom of plastic culture box. (E) Root induction in *E. californicum* on MS medium with 1 mg/l IBA. (F) Growth and development of *E. trichocalyx* plant in vitro. (G) *E. californicum* plant in a pot, 2 weeks after transfer. (H) *E. trichocalyx* plant in a pot, 4 weeks after transfer.

Plants have emerged as modern efficient systems for production and delivery of recombinant products, including, but not limited to, microbicides and antigens. When applied on a mucosal surface, preparations of this herb have a capacity to hold aqueous components in contact with mucosal cells that may facilitate adherence of pharmaceuticals to the mucosa. Accordingly, Yerba Santa may be useful as a vehicle for effective delivery of recombinant molecules, such as recombinant microbicides or vaccines, to body surfaces including mucosal surfaces, including, for example, intranasal and oral surfaces. A benefit of using plants for production of recombinant drugs is that they allow direct mucosal (and thus needle-free) administration of the pharmaceutical. For mucosal delivery of a vaccine antigen to a subject, the extended mucosal exposure to such a plant-based vaccine may significantly increase immune response in the subject. Microbicides reduce the infectivity of microbes, such as viruses or bacteria, by averting infection at the mucosal surfaces. Accordingly, a plant based delivery system that is directly applied to mucosal surfaces is ideally suited for the administration of microbicides.

Yerba Santa is suitable for human consumption, has been used in medicine for centuries, and is widely used in the food industry. According to certain aspects of the invention, modern plant biotechnology techniques have been developed for this valuable medicinal plant, including the development of transgenic Yerba Santa plants. In certain embodiments, in vitro propagation, regeneration and transformation systems are provided for Yerba Santa species. In certain aspects, cell culture technologies are provided for Yerba Santa that may offer economically favorable methods for production of large amounts of recombinant pharmaceuticals. For example, cell suspensions may be used to produce large amounts of biopharmaceuticals in bioreactors under controlled conditions to achieve uniform, high quality products.

One aspect of the present invention is a transgenic plant; preferably the plant is a member of the genus *Eriodictyon*. Preferably, the plant is *E. californicum, E. trichocalyx* or *E. sessilifolium.*

In certain embodiments, the invention relates to a recombinant protein expressed by a transgenic plant according to aspects of the invention.

As used herein, a "recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. This protein may include an entire (full-length) protein or a polypeptide molecule, or may comprise a protein or polypeptide fragment suitable for a particular purpose. Preferably, the recombinant proteins expressed by the transgenic plant are suitable for use as pharmaceuticals, including, but not limited to, antigens, microbicides, antibodies, hormones, enzymes, blood components, including, but not limited to, coagulation factors, interferons, and anticoagulants.

As used herein, "antigen" may include a single antigen or a plurality of antigens as long as at least one antigen is included which, when administered in a sufficient amount, can induce an immune response in a subject. The term "antigen" also includes any portion of an antigen, e.g., the epitope, which can induce an immune response. Preferably, the one or more antigens will produce a sufficient immune response to confer resistance to infection upon the recipient of the antigen. Examples of immunogenic or antigenic molecules that may be useful include, without limitation, viral antigens such as the entirety or portions of: Hepatitis virus B surface antigen, Malaria parasite antigen, Influenza A H1N1 antigen, Rabies virus glycoprotein, *Escherichia coli* heat-labile enterotoxin, Human rhinovirus 14 (HRV-14), human immunodeficiency virus type (HIV-1) epitopes, Norwalk virus capsid protein, Diabetes-associated autoantigen, Mink Enteritis Virus epitope, Foot and mouth disease virus VP1 structural protein, Cholera toxin B subunit, Human insulin-Cholera toxin B subunit fusion protein, Human cytomegalovirus glycoprotein B, *S. mutans*, respiratory syncytial virus antigens (F1, F2, G), tetanus toxin fragment C, diphtheria toxin, S1 subunit of pertussis toxin and SARS S-glycoprotein.

In certain embodiments, the protein expressed by the transgenic plant comprises an antigen protein, preferably a viral protein, more preferably an avian influenza HA1 antigen.

As used herein, "microbicide" refers to any compound or substance whose purpose is to reduce the infectivity of microbes, such as viruses or bacterial. Examples of microbicides that may be useful include, without limitation, griffithsin, the fusion inhibitor C52, RANTES analogue PSC-RANTES, and lectin cyanovirin-N (CV-N).

In certain embodiments, the recombinant protein expressed by the transgenic plant comprises a microbicide, preferably an antiretroviral microbicide, more preferably an HIV entry inhibitor, even more preferably griffithsin. As used herein, "griffithsin", which has been shown to be a highly potent HIV entry inhibitor, refers to a 121-amino-acid protein isolated from the red algae Griffithsia or active mutants or fragments thereof. Griffithsin. Mori T, O'Keefe B R, Sowder R C, et al. (2005), "Isolation and characterization of griffithsin, a novel HIV-inactivating protein, from the red alga Griffithsia sp", J. Biol. Chem. 280 (10): 9345-53.

Examples of antibodies that may be useful include, without limitation, monoclonal antibodies (mAbs) and secretory IgA (sigA). Antibody formats may include, without limitation, full-size, Fab fragments, single-chain antibody fragments, bi-specific scFv fragments, membrane anchored scFv, chimeric antibodies and humanized antibodies.

Examples of hormones that may be useful include, but are not limited to insulin, somatotropin, and erythropoietin.

Examples of enzymes that may be useful include, without limitation, α-1-antitrypsin, aprotinin, Antiotensin-1-converting enzyme, and Glucocerebrosidase Examples of blood components that may be useful include, without limitation, serum albumin, including human serum albumin, and hemoglobin.

Examples of interferons that may be useful include, without limitation, interferon-α.

Examples of anticoagulants that may be useful include, without limitation, protein C (serum protease) and hirudin.

In certain embodiments, the invention relates to methods for producing recombinant proteins in transgenic plants comprising the steps of: constructing a plasmid vector or a DNA fragment by operably linking a DNA molecule comprising a sequence encoding a protein to a promoter capable of directing the expression of the protein in the plant; transforming a plant cell with the plasmid vector or DNA fragment to create a transgenic plant cell; and recovering the protein expressed in the plant cell for use. Preferably, the plant is a member of the genus *Eriodictyon*. Preferably, the plant is *E. californicum, E. trichocalyx*, or *E. sessilifolium*. Preferably, the recombinant proteins are suitable for use as pharmaceuticals, including, but not limited to, antigens; microbicides; antibodies; hormones; enzymes; blood components, including, but not limited to, coagulation factors; interferons, and anticoagulants.

Exogenous DNA constructs used for transforming plant cells will comprise the coding sequence of recombinant protein desired to be expressed and usually other elements such as, but not limited to introns, 5' and 3' untranslated regions, and promoters. In certain embodiments, the utilization of a strong promoter, such as the Rubisco promoter operably linked to the coding sequence of the desired recombinant protein, provides large amounts of recombinant protein in Yerba Santa leaves.

As is well known in the art, DNA constructs for use in transforming plants and expressing a coding sequence typically also comprise other regulatory elements in addition to a promoter, such as but not limited to 3' untranslated regions (such as polyadenylation sites), transit or signal peptides and marker coding sequences elements.

During transformation, exogenous DNA may be introduced randomly, i.e. at a non-specific location, in the plant genome. In some cases, it may be useful to target an exogenous DNA insertion in order to achieve site-specific integration, e.g. to replace an existing gene sequence or region in the genome. In some other cases it may be useful to target an exogenous DNA integration into the genome at a predetermined site from which it is known that gene expression occurs.

In practice DNA is introduced into only a small percentage of target cells in any one experiment. Marker genes are used to provide an efficient system for identification of those cells that are stably transformed by receiving and integrating an exogenous DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring coding sequence has been integrated and expressed at sufficient levels to permit cell survival. Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS; CP4).

Means for transforming plant cells are well known in the art. Suitable methods include any method by which DNA can be introduced into a cell, such as by *Agrobacterium* mediated transformation, via bombardment by DNA coated particles, direct delivery of DNA such as, for example, by PEG-mediated transformation of protoplasts, by desiccation/inhibition-mediated DNA uptake, by electroporation, or by agitation with silicon carbide fibers.

In certain embodiments, the methods further comprise regenerating a transgenic plant from the transgenic plant cell. This step is performed prior to recovering a recombinant protein expressed by the transgenic plant. In certain aspects, the methods may comprise a recovery step that further comprises obtaining an extract of the plant cell. In certain aspects, the methods may comprise harvesting material from at least a portion of the transgenic plant. In certain embodiments, at least a portion of the material harvested from the transgenic plant is edible.

Preferably, the methods directed to transforming a plant cell may comprise the use of an *Agrobacterium* system.

In certain embodiments of the invention, a recombinant protein is expressed in a transgenic plant, at least a portion of which plant is edible. In certain aspects, the recombinant protein may be administered to a subject by oral administration, wherein a portion of the plant expressing the recombinant protein is ingested by the subject, such that an effective amount of the recombinant protein is delivered to the subject.

The invention relates, in certain aspects to a method for constructing a transgenic plant cell comprising the steps of: constructing a plasmid vector or a DNA fragment by operably linking a DNA molecule, the DNA molecule comprising a sequence encoding a protein, to a promoter capable of directing the synthesis of the protein in the plant; and transforming a plant cell with the plasmid vector or DNA fragment; preferably, the plant is a member of the genus *Eriodictyon*. In certain embodiments, the plant is preferably *E. californicum, E. trichocalyx*, or *E. sessilifolium.*

Preferably, the method of transforming the plant cell comprises the use of an *Agrobacterium* system.

In certain embodiments, the method may further comprise regenerating transgenic plants from the transgenic plant cell.

In certain aspects, the present invention relates to several factors that influence efficiency of *Agrobacterium*-mediated transformation. For example, the invention relates to a method for transforming a plant tissue comprising the steps of: inoculating a transformable plant tissue with an Agrobacterium suspension diluted to about $OD_{600}$ 0.005 to 0.5, the *Agrobacterium* containing at least one genetic component encoding a desired protein capable of being transferred to the transformable plant tissue and of directing the expression of the desired protein in the plant tissue; co-cultivating the plant tissue with the *Agrobacterium*; transferring the plant tissue to recovery media containing an antibiotic for eliminating the *Agrobacterium*; and selecting transformed plant tissue. In certain embodiments, the plant tissue is from a plant species of the genus *Eriodictyon*, preferably *Eriodictyon californicum, Eriodictyon trichocalyx* and *Eriodictyon sessilifolium.*

As used herein, "$OD_{600}$" means the optical density measure at a wavelength of 600 nanometers. In a preferred embodiment, the inoculating step is performed with an *Agrobacterium* suspension diluted to about $OD_{600}$ 0.01 to 0.05, more preferably about $OD_{600}$ 0.03.

In certain embodiments, the length or temperature of the steps in the transforming method must be precisely monitored to achieve transformed plants. For example, the inoculating step may be performed for about 1 to 30 minutes, preferably for about 5 to 15 minutes, and more preferably for about 10 minutes. Likewise, the co-cultivating step may be performed for about 1 to 4 days, preferably for about 2 days, at about 20 to 25° C. Finally, the plant tissue may remain in the recovery media for about 5 to 20 days, more preferably for about 10 days.

In other embodiments, the method for transforming a plant tissue further comprises transferring the plant tissue to media containing successively higher concentrations of a selective agent. Typical selective agents include but are not limited to antibiotics such as kanamycin, geneticin, paromomycin or other chemicals such as glyphosate. In one embodiment, the selective agent is kanamycin and the genetic component of the *Agrobacterim* is capable of conferring kanamycin resistance to the plant tissue.

The present invention, in certain aspects, also relates to methods for producing a recombinant protein in a transgenic plant of the genus *Eriodictyon* comprising the steps of: providing a transgenic plant that has been regenerated from a transformed plant cell or tissue of the genus *Eriodictyon* and that expresses a recombinant protein; and recovering the protein expressed in the transgenic plant. Preferably, the plant is from the species of *E. californicum, E. trichocalyx*, or *E. sessilifolium*. In certain embodiments, the recovery step further comprises obtaining an extract of the transgenic plant or harvesting material from at least a portion of the transgenic plant such as an edible portion of the plant.

The method of producing a recombinant protein in a transgenic plant, in certain embodiments may include using an *Agrobacterium* system, as described herein, to transform the plant cell or tissue.

Preferably, the recombinant proteins produced by this method are suitable for use as pharmaceuticals, including, but not limited to, antigens; microbicides; antibodies; hormones; enzymes; blood components, including, but not limited to, coagulation factors; interferons, and anticoagulants.

In certain embodiments, the method involves producing an antigen protein, preferably a viral protein, more preferably an avian influenza HA1 antigen.

In other embodiments, the method involves producing a microbicide, preferably an antiretroviral microbicide, more preferably an HIV entry inhibitor, even more preferably griffithsin.

The present invention, in certain aspects, also provides methods of delivering a recombinant protein to a subject comprising providing harvested material from a transgenic plant of the genus *Eriodictyon* that expresses a recombinant protein; and administering the harvested material to the subject in an amount necessary to deliver an effective amount of the recombinant protein.

In certain embodiments, the method of administration comprises delivery to the subject of an edible portion of the transgenic plant expressing a recombinant protein. In other embodiments, the method of administration may comprise mucosal delivery to the subject of recombinant protein or material containing such protein harvested from a transgenic plant produced according to an aspect of the invention.

As used herein, the term "subject" is used to mean an animal, preferably a mammal, including a human. The terms "patient" and "subject" may be used interchangeably. Thus, certain embodiments of the invention are directed to appropriate dosage forms useful in the administration of active pharmaceutical ingredients to a subject.

As used herein, "mucosal surface" includes, without limitation, nasal, oral, lingual, sub-lingual, buccal, gingival, palatal, vaginal, ocular, auditory, pulmonary tract, urethral, and rectal surfaces. Certain embodiments of the invention relate to compositions and methods for administration of pharmaceutical agents to a mucosal surface in a subject.

A composition comprising a recombinant protein produced according to an aspect of the invention may be applied to any mucosal surface as deemed appropriate for the delivery thereof, including vaginal, rectal, and ocular surfaces. In certain preferred embodiments, the method of delivery the mucosal surface is to an intranasal or oral surface of the subject. Preferably, the oral surface may include, but is not limited to, lingual, sub-lingual, buccal, gingival, and palatal surfaces.

In certain preferred embodiments, the recombinant protein comprises an antigen, preferably a viral antigen, more preferably an avian influenza HA1 antigen. In this embodiment, the harvested material which contains the expressed antigen is administered in an amount sufficient to induce an immune response in the subject. The immune response may include the induction of cytotoxic T lymphocytes or the generation of antibodies. Preferably, the delivery of the antigen to the subject will produce a sufficient immune response to confer resistance to infection upon the subject. In any event, the method may be used to generate antibodies to the antigen which may be used to aid in the purification of the antigen. Additionally, any generated antibodies may be useful in the detection of the virus from which the antigen is derived.

In other embodiments, the recombinant protein is a microbicide, preferably an antiretroviral microbicide, more preferably an HIV entry inhibitor, even more preferably griffithsin. In this embodiment, the harvested material which contains the expressed microbicide is administered in an amount sufficient to provide a prophylactic effect. For example, harvested material from Yerba Santa expressing the microbicide griffithsin may be administered to the mucosal surfaces (such as the vaginal or rectal mucosa) of subjects to protect these surfaces from HIV transmission.

The present invention, in certain aspects, also provides methods of propagating a plant in vitro, wherein the plant is preferably a member of the genus *Eriodictyon*, the method comprising the steps of: excising a stem segment, preferably a segment having a node; and incubating the segment in a growth medium, preferably MS medium, the medium preferably comprising a cytokinin, more preferably zeatin; whereby the segment produces a shoot. Preferably, the plant so propagated is *E. californicum, E. trichocalyx*, or *E. sessilifolium.*

As used herein, "cytokinins" refer to a class of plant hormones that promote cell division. Examples of cytokinins include the adenine-type cytokinins, kinetin, zeatin, benzylaminopurine (BAP); and the phenylurea-type cytokinins, diphenylurea and thidiazuron.

In certain embodiments, the methods may further comprise the steps of: excising a shoot; and, preferably, incubating the excised shoot in medium, preferably MS medium, the medium preferably comprising an auxin, more preferably indole-3-butyric acid; whereby the shoot produces a root.

As used herein, "auxins" refer to a class of plant hormones that control cell expansion. Examples of auxins include the naturally occurring auxins, 4-chloro-indoleacetic acid, phenylacetic acid (PAA), and indole-3-butyric acid (IBA), indole-3-acetic acid (IAA); and the synthetic auxins, naphthaleneacetic acid (NAA) and 2,4-dichlorophenoxyacetic acid (2,4-D).

The methods of the invention may further comprise the steps of: incubating the shoot, preferably for at least three weeks, in culture medium, whereby the shoot produces a leaf. The methods may further comprise the steps of: cutting a segment from the leaf; placing the segment in a culture medium; and incubating the segment in the dark, whereby the segment develops callus tissue. Preferably, the medium is MS medium. Preferably, the medium at least one of BAP, NAA and 2,4-D. More preferably, the medium comprises each of BAP, NAA, and 2,4-D.

In certain aspects, the invention relates to methods for rapid mass propagation of three Yerba Santa species in vitro, root induction, induction of cell suspensions, regeneration, transformation and transfer of plants to greenhouse conditions. Additionally, methods for the production of callus tissues for all three species and for the establishment of tissue culture, including fast growing cell suspensions, are provided. Rapid and high frequency regeneration from leaf explants is efficient for these three Yerba Santa species. In certain embodiments, an efficient transformation protocol is provided and used for the production of an avian flu antigen or griffithsin in Yerba Santa leaf tissues. Overall these results provide additional opportunities to utilize and expand on the beneficial properties of this unique medicinal herb.

In certain aspects, the invention relates to methods of producing a cell suspension culture of a plant, preferably a plant that is a member of the genus *Eriodictyon*, the method comprising the steps of: excising a portion of the callus tissue produced according to certain aspects of the invention; placing the callus tissue in a liquid medium, preferably MS medium, the medium preferably comprising 2,4-D; and incubating the suspension in the dark with agitation.

In certain embodiments, the invention relates to protocols for in vitro propagation, callus induction, shoot regeneration, establishment of a rapid growing cell suspension culture, and propagation in greenhouse conditions for Yerba Santa. Rapid and high frequency regeneration from leaf explants (via shoot organogenesis) was efficient for all tested Yerba Santa species. An *Agrobacterium*-mediated transformation protocol was established. In certain aspects, transformation conditions are provided for successful production of transgenic Yerba Santa, including, for example, the use of a precultivation period, low concentration of *Agrobacterium* inoculums, and a multi-step selection procedure.

Yerba Santa species demonstrated several challenges in tissue culture and transformation experiments including browning of explants on different media, difficulties with root induction, high levels of necrosis after co-cultivation with *Agrobacterium* and selection procedures. Some of these difficulties are often encountered for other medicinal plants. In certain embodiments of the invention, efficient tissue culture and transformation protocols for Yerba Santa are provided which may potentially find use with other recalcitrant medicinal plants.

Certain aspects of the invention relate to rapid mass propagation of three species of Yerba Santa. In vitro propagation may permit the production of pathogen-free material. Propagation from nodal stem segments may yield plants that are genetically identical with the donor plants. In certain aspects, techniques described herein may provide methods for rapid propagation on a commercial scale of these medicinally important plant species.

According to particular aspects of the invention, Yerba Santa cell suspensions are provided, which are demonstrated to be very fast growing and not to contain large aggregates. This overcomes some difficulties that may be encountered in developing and maintaining an efficient cell suspension from different plant species; including a slow rate of cell growth and the formation of large clumps during the culture period.

These plant-cell—suspension cultures may be used for the production of recombinant proteins, including, but not limited to, vaccines (Fischer et al., (1999) *Journal of Immunol Methods* 226: 1-10); in certain embodiments, this production may be performed under controlled certified conditions. The Yerba Santa suspensions described herein have very good growth rates, comparable to other fast-growing suspensions described in the relevant literature.

The following examples are provided for the purpose of further illustrating the present invention but are by no means intended to limit the same.

EXAMPLES

Materials and Methods

Plant Material and Propagation In Vitro

Plant material of three Yerba Santa species (*Eriodictyon californicum, Eriodictyon sessilifolium*, and *Eriodictyon trichocalyx*) are obtained from Rancho Santa Ana Botanic Garden (Claremont, Calif.) and Las Pilitas Nursery (Santa Margarita, Calif.). Segments of stem are excised from Yerba Santa plants, washed thoroughly under running tap water, and then are dipped in 70% ethanol for 1 min, followed by a 25 min soak in a 1.2% solution of commercial sodium hypochlorite. After rinsing 3 times with sterile distilled water, segments with 1 or 2 nodes are transferred to Phytatrays containing MSP media. Phytatrays are sealed with Parafilm and incubated in a growth chamber at 24° C. at 16 h-light/8 h-dark photoperiods with light intensity of 40 uE/m2/S1. In vitro cultures are maintained by transferring 1-cm-long shoot segments at 5-6 week intervals onto fresh medium. For root induction 3-4 cm shoots are placed in root induction media MSRI (Table 1). Rooted plants are transferred to pods containing soil Metromix and sand (3:1).

TABLE 1

Media for tissue culture and transformation experiments

| Name | Media composition |
|---|---|
| MS0 | Basic MS basal medium with 3% sucrose, 0.8% agar |
| MSP | MS0 with 1 mg/l zeatin |
| MSC-1 | MS0 with 0.3 mg/l BAP, 0.5 mg/l NAA, 1 mg/l 2,4-D |
| MSC-2 | MS0 with 1 mg/l 2,4-D |
| MSS | MS with 3% sucrose, 0.5 mg/l 2,4-D (liquid) |
| MSR | MS with 3% sucrose, 1 mg/l zeatin, 0.1 mg/l NAA, 5 mg/l silver nitrate 0.9% agar |
| MSRI | MS0 with 1 mg/l IBA |
| MST-1 | MS0 with 100 μM acetosyringone |
| MST-2 | MSR with 300 mg/l timentin |
| MST-3 | MSR with 50 mg/l kanamycin, 300 mg/l timentin |
| MST-4 | MSR with 70 mg/l kanamycin, 250 mg/l timentin |
| MST-5 | MSR with 100 mg/l kanamycin, 200 mg/l timentin |
| MST-6 | MS0 with 1 mg/l IBA, 150 mg/l timentin |

Callus Initiation, Cell Suspensions

Leaf segments (0.5-0.7 cm) are cut from the 3-4 week-old in vitro propagating shoots from three Yerba Santa species and placed in Petri dishes (100×15 mm) on MSC-1 medium for induction of callus. Plates are incubated in the darkness at 24° C. for 4-6 weeks. Well developed calli are selected and transferred to MSC-2 medium. Callus tissue is maintained on MSC-2 medium at 3- to 4-week intervals. All the plates with callus cultures are incubated in the dark at 24-25° C. Friable callus is used for initiation of cell suspensions. Approximately 1 g fresh weight of callus tissue are transferred into 50 ml of medium MSS medium in sterile 250 ml conical flasks. Cell cultures are grown on a rotary shaker at 130 rpm in the dark at 25° C. In order to maintain suspension culture a portion (2-3 ml) of liquid suspension cells are transferred to fresh MSS medium at 10-14 day-intervals.

Generation of Transgenic Plants

Leaf segments (0.5-0.7 cm) are cut from the 3-4 week-old in vitro propagating shoots of three Yerba Santa species and placed in Petri dishes (100×15 mm) on MSR medium. Ten to twelve explants per Petri dish are cultivated for 6 weeks and tested for shoot regeneration efficiency. *Agrobacterium tumefaciens* strain LBA 4404 is grown overnight in LB medium supplemented with appropriate antibiotics at 28° C. Binary vector pBIN-Plus (ImpactVector, Wageningen, the Netherlands) harboring an expression cassette of avian flu HA1 antigen fused with Fc and driven by the Rubisco promoter is used. The expression cassette contains the c-Myc and His6 tags at the C-terminus. The vector also contains the npt II gene for kanamycin selection of transgenic plants. Leaf segments are inoculated with *Agrobacterium* suspension ($OD_{600}$ 0.5, 0.3, 0.1 or 0.03) for 10 min. After blotting dry with sterile filter paper, explants are transferred to MST-1 co-cultivation medium supplemented with acetosyringone (Table 1) and incubated in the dark for 2 or 3 days at 24° C. To determine the effect of preculture on transformation efficiency, explants are cultured for 2, 3 or 4 days on MSC-1 medium before inoculation with *Agrobacterium*. After co-cultivation, explants are transferred to MST-2 medium without selection for 7, 10 and 14 days and then transferred to MST-3 regeneration selection medium with 50 mg/l kanamycin. After 3 weeks, regenerated green shoots are transferred to second selection medium MST-4 with increased concentration of kanamycin (70 mg/l), and after an additional 3 weeks explants are transferred to third selection medium MST-5 with high kanamycin concentration (100 mg/l). Putative transgenic shoots are excised and transferred to rooting medium (MSRI supplemented with 150 mg/l timentin). Plantlets with roots are transferred to pots containing a mixture of soil and sand.

Example 1

In Vitro Propagation and Root Induction

For establishment of in vitro cultures stem segments with nodes of three Yerba Santa species (*Eriodictyon californicum, Eriodictyon sessilifolium*, and *Eriodictyon trichocalyx*) are used as primary explants. They are washed, surface sterilized and placed on MS medium (Murashige T& Skoog F. (1962) Physiol Plant 15:473-497) supplemented with different cytokinins: $N^6$-benzylaminopurine (BAP), zeatin, and kinetin. All three Yerba Santa species propagate in vitro most efficiently on basal MS medium supplemented with 1 mg/l zeatin. During 6 weeks a significant number of shoots are produced for all three species. Comparison of the shoot propagation capacity of three species of Yerba Santa demonstrates the highest efficiency in *E. trichocalyx* (FIGS. 1, A and B), about 8-10 shoots are produced from each explant in 4-5 weeks. A single explant of this species can produce thousands of shoots in 3-4 months.

Individual shoots are excised and transferred to hormone-free medium for rooting. Yerba Santa species demonstrate different root formation capacities. *E. sessilifolium* start to form roots after 7-10 days on media without hormones (FIG. 1C), whereas *E. californicum* and *E. trichocalyx* show significant difficulties with root formation. Therefore media with different auxins are tested for stimulation of root formation: naphthalene acetic acid (NAA), indole-3-acetic acid (IAA), and indole-3-butyric acid (IBA). The best root development for both cultivars is recorded on medium supplemented with 1 mg/l IBA (FIGS. 1, D and E), however some of the shoots are not able to produce roots. After testing shoots of different size and development, it appears that large (3-4 cm), healthy and well developed shoots of *E. californicum* and *E. trichocalyx* are capable of producing roots. Rooted plants (FIG. 1F) are transferred to pods with mixture of soil (Metromix) and sand (3:1) (FIGS. 1G and 1H). Morphology of the micropropagated plants are identical to that of normal propagated plants.

Example 2

Establishment of Cell Suspensions

To obtain a rapidly growing cell suspension culture, three Yerba Santa species are screened for callus induction and cultivation. Callus tissues are initiated for all three Yerba Santa species from leaf explants on callus induction media MSC-1 after 4-6 weeks of incubation in darkness. For future propagation, callus tissues are transferred to MSC-2 medium. After 6-8 weeks of cultivation on MSC-2 medium, the callus of *E. trichocalyx* showed the best growth capacities (FIG. 2A) *E. californicum* also demonstrated good growth capacity, however some part of the callus tissues showed browning (FIG. 2B).

Figure 2:
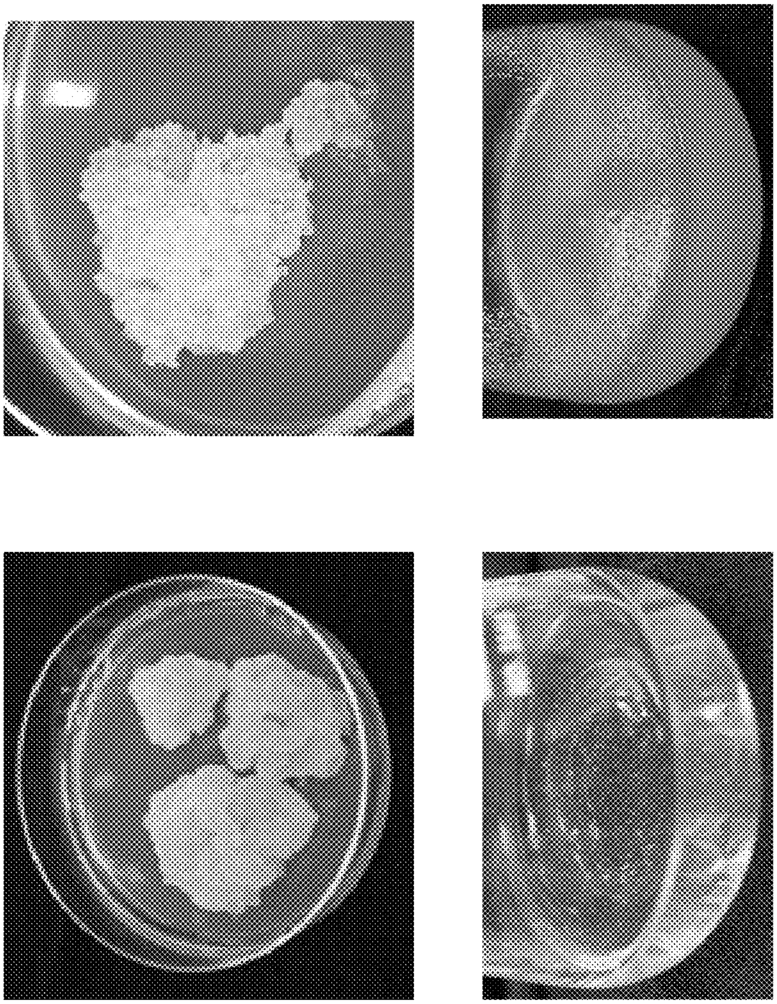
FIG. 2 illustrates Yerba Santa callus and cell suspension cultures. (A) Callus propagation on MS medium with 1 mg/l 2.4-D (*E. trichocalyx*). (B) Callus propagation on MS medium with 1 mg/l 2,4-D (*E. californicum*). (C) Cell suspension (*E. trichocalyx*), 1 day in liquid MS medium with 0.5 mg/l 2,4-D. (D) Cell suspension (*E. trichocalyx*) after 2 weeks in liquid MS medium with 0.5 mg/l 2,4-D.
Figure 3:
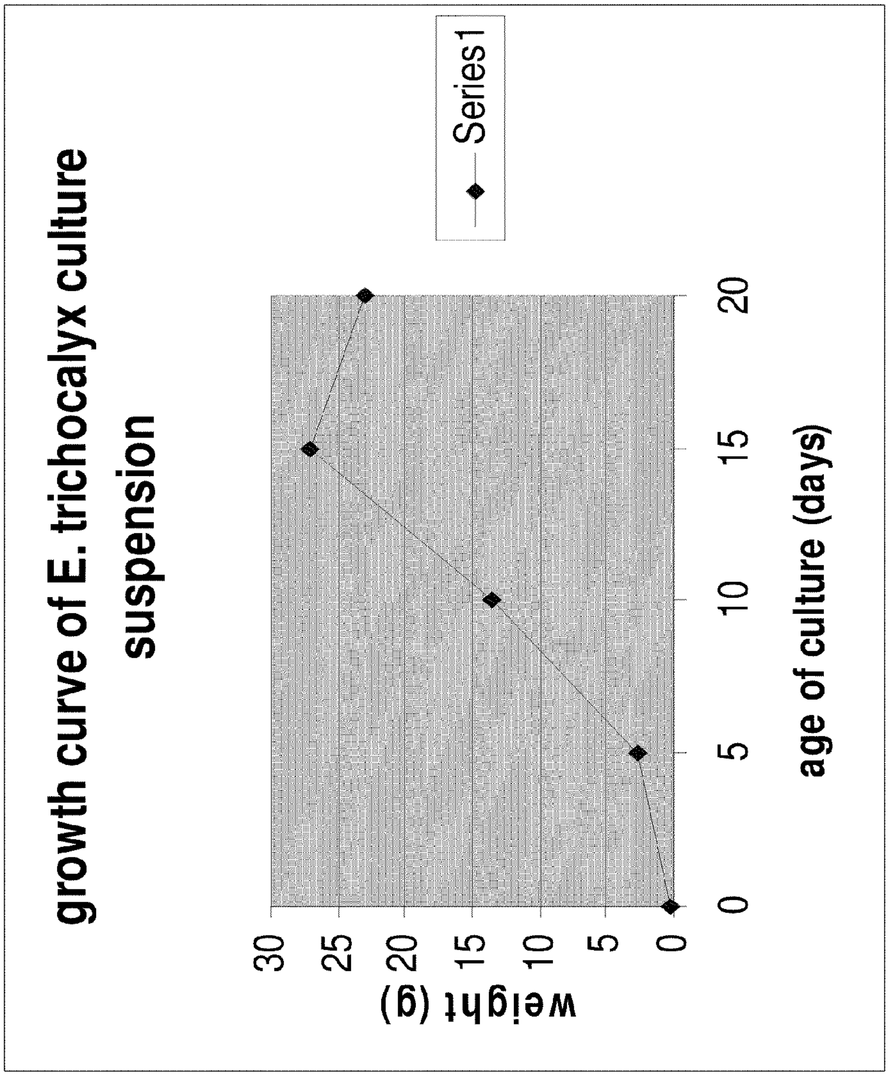
FIG. 3 is a graph illustrating the growth rate of a Yerba Santa *E. trichocalyx* cell suspension.

Cell suspensions of Yerba Santa species are established from callus tissues in liquid media MSS. *E. trichocalyx* show the best results, including fast growth rates of cells, no browning of cells, and mild cell aggregations (FIGS. 2C and 2D). The *E. trichocalyx* cell suspension is very fast growing: about a 10-12-fold increase in cell volume is achieved in 5-7 days. (FIG. 3). These results are comparable with most fast growing cell suspension of other plant species (Fischer R & Schillberg S (eds) (2004) Molecular Farming. Plant-made Pharmaceuticals and Technical Proteins Wiley-VCH Verlag GmbH & Co. Weinbeim) and can provide a very efficient system for the production of vaccines and other recombinant proteins.

Example 3

Transformation of Yerba Santa

Figure 4:
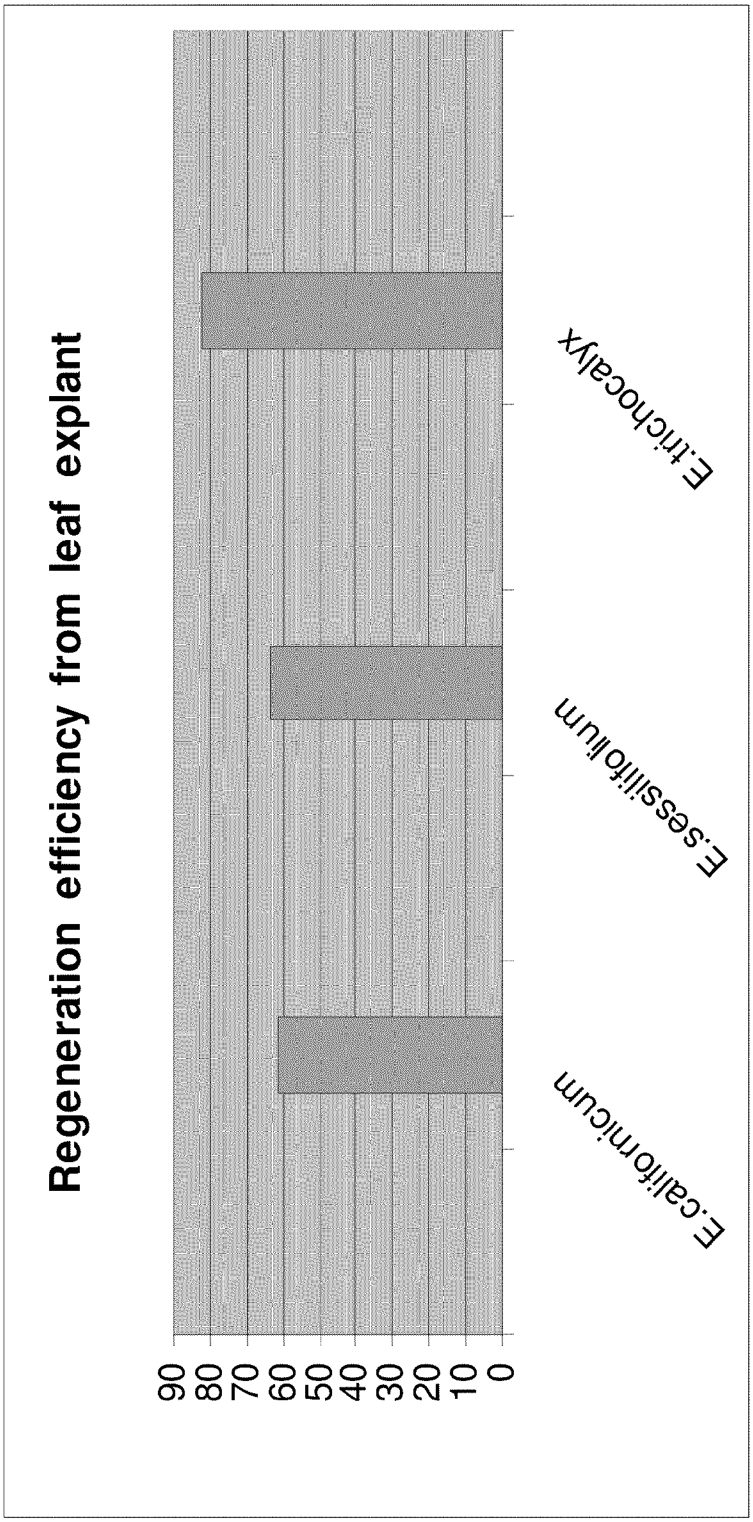
FIG. 4 is a graph illustrating shoot regeneration efficiency in three Yerba Santa species. Regeneration efficiency is expressed as the percent of explants producing shoots on MSR medium during 6 weeks.
Figure 5:
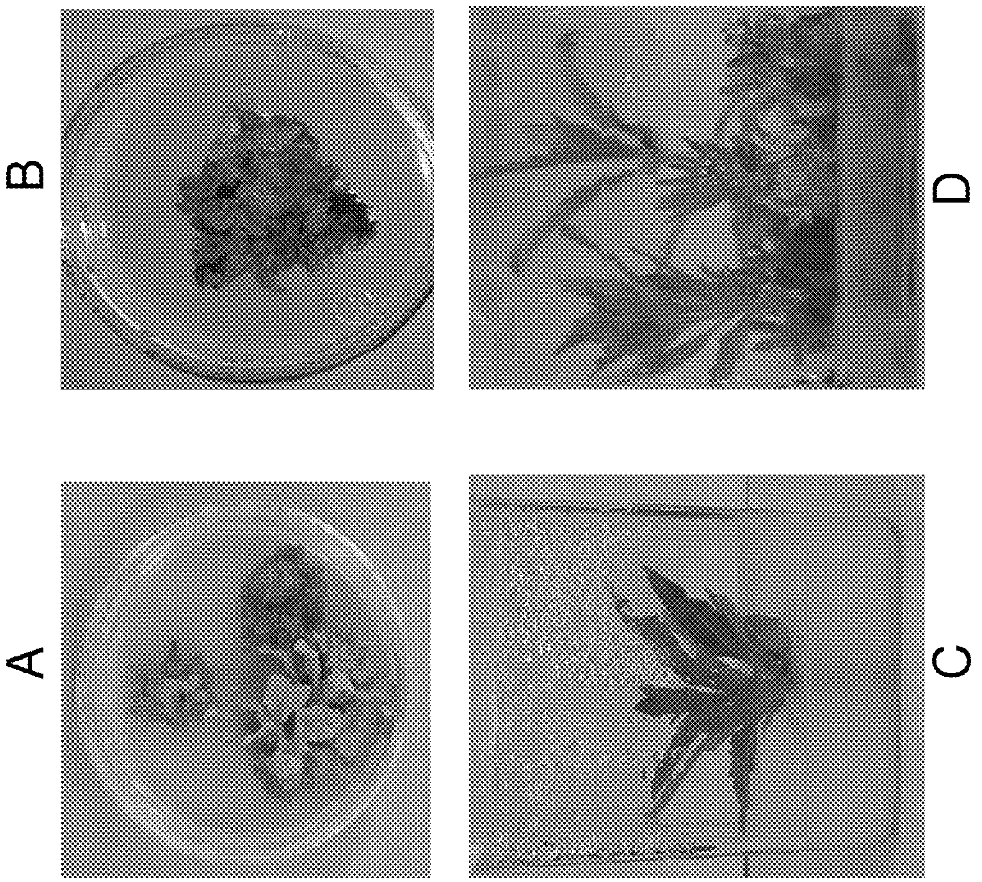
FIG. 5 illustrates an assessment of regeneration and transformation procedures for Yerba Santa (*E. trichocalyx*.) (A) Regeneration through callus formation; (B) Direct regeneration from leaf explant on MSR medium; (C) Transgenic plant expressing Avian flu antigen on MST-5 medium containing 100 mg/l kanamycin; (D) Multiplication of transgenic line on MSP medium.

As a first step in the development of an efficient transformation system, the development of an efficient regeneration system is initiated. Preliminary experiments using different media compositions and types of explants indicate that shoots from several Yerba Santa species regenerate most efficiently on MSR medium (Table 1) and that leaf segments have the best regeneration potential. During 5-6 weeks leaf explants produce multiple shoots on MSR medium through direct regeneration without callus formation. Comparison of the regeneration capacity of three species (*E. californicum, E. sessilifolium*, and *E. trichocalyx*) reveal the highest regeneration efficiency in *E. trichocalyx* leaf segments reaching 75%-82% (FIG. 4; FIGS. 5A and 5B). Based on the results of regeneration experiments, leaf segments of *E. trichocalyx* are chosen as explants for transformation experiments.

Preliminary transformation experiments reveal several challenges associated with inoculation and selection for Yerba Santa species. In the first series of experiments, the efficiency of the inoculation procedure is tested. The exposure of leaf explants to *Agrobacterium* culture at $OD_{600}$ 0.5 cause severe necrosis in most of the treated Yerba Santa explants. Pre-cultivation of *E. trichocalyx* leaf explants is tested for 2, 3 and 5 days before inoculation with *Agrobacterium* $OD_{600}$0.5. However, this approach does not appear to decrease the number of browning tissues after inoculation and co-cultivation procedures. In an effort to reduce necrosis of explants in response to *Agrobacteria*, the *Agrobacteria* suspension is diluted to $OD_{600}$ 0.3, 0.1, and then finally to 0.03. Inoculation of leaf segments with a suspension diluted to 0.03 significantly decreases the level of necrosis. In the same set of experiments, it is demonstrated that 2 days of co-cultivation significantly decreased necrosis, as compared to 3 days. The addition of polyvinylpyrrolidone (250 mg/l) and increasing the agar concentration in the media also prove to be beneficial.

Figure 6:
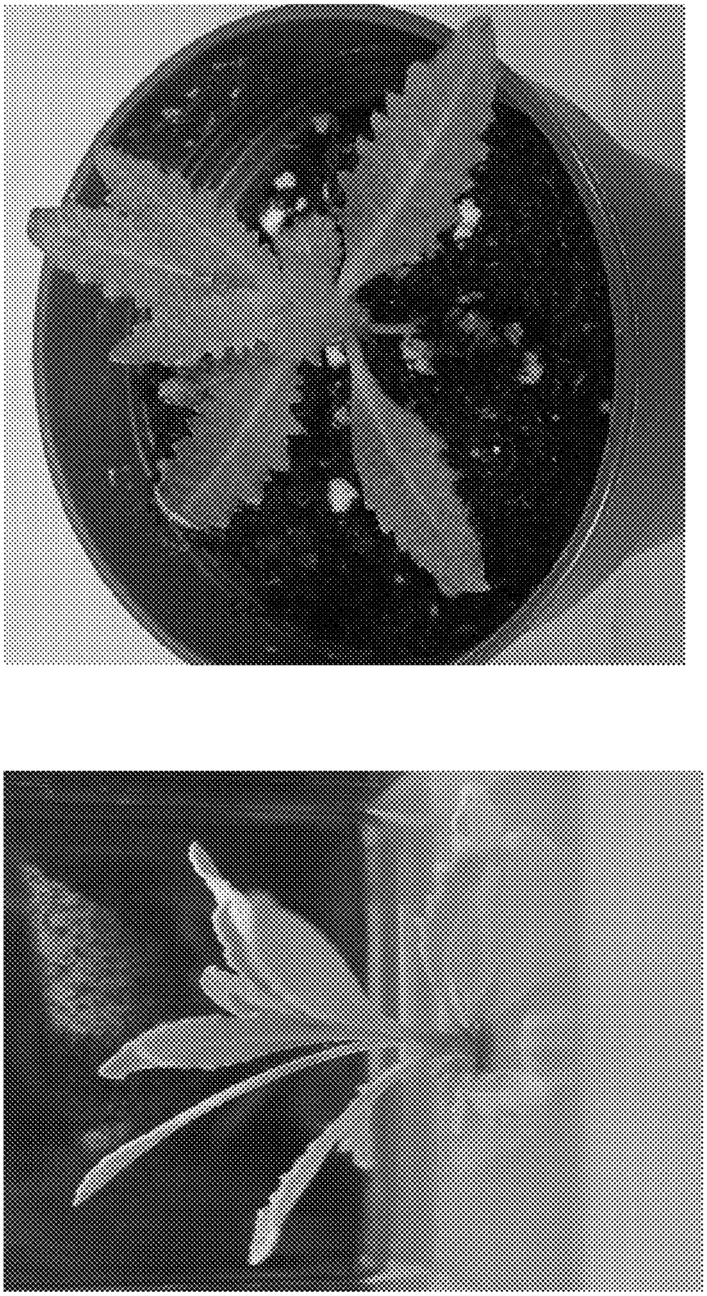
FIG. 6 illustrates a transgenic Yerba Santa (*E. trichocalyx*) expressing Avian flu antigen. (A) Transgenic plant on root induction medium; (B) Transgenic plant in a pot.

Several selection schemas are tested. No transgenic plants are recovered when selection is started immediately after co-cultivation. Therefore, the effect of a delay period is tested, during which explants are kept in MST-2 non-selection medium supplemented with timentin for *Agrobacterium* elimination for 7, 10 or 14 days. Transgenic shoot regeneration from explants is highest when leaf explants are left on MST-2 medium for 10 days, then explants are transferred to selection medium. Among different selection systems tested the best results are obtained with a 3-step selection procedure with a gradually increasing concentration of kanamycin in the selection regeneration media. Use of a relatively low concentration of kanamycin (50 mg/l) in the first selection media reveals good survival of tissues and a large percent of escapes. After 3 weeks, the explants are transferred to a second selection medium containing 70 mg/l kanamycin and finally to a selection medium with 100 mg/l kanamycin (FIG. 5C). When shoots reach 3-4 cm in length (FIG. 5D), they are transferred to root induction media MSR1 with addition of 150 mg/l timentin (FIG. 6A). Rooted plants are transferred to pods with mixture of soil and sand (FIG. 6B).

Example 4

Expression of Avian Influenza Antigen

Figure 7:
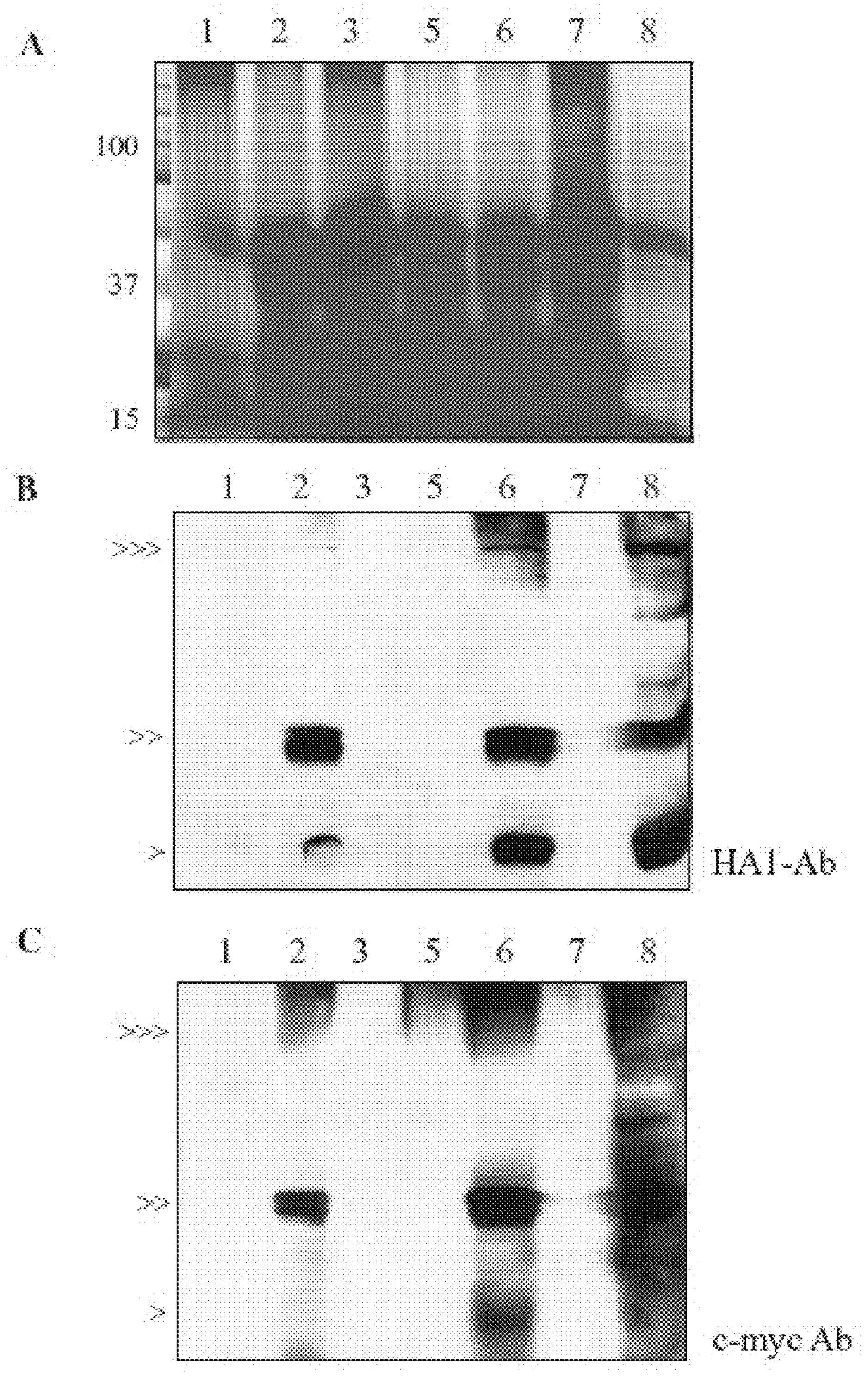
FIG. 7 is a Western blot analysis of transgenic Yerba Santa plants showing expression of recombinant HA1 antigen. (A) SDS/PAGE. (B) Western blot using HA1 antigen-specific antibodies. (C) Western blot using c-Myc antibodies.

Leaf tissues of transgenic plants are tested for level of expression of avian influenza antigen. Western blot analysis with C-myc antibodies reveals a protein band of the expected molecular size in the leaf tissue of transgenic plants (FIG. 7). The morphology of the transgenic plants is identical to that of non-transgenic plants (FIG. 6B and FIG. 1H).

Example 5

Immunological Assessment of Plant-Expressed Avian Influenza Antigen in Mice

Groups of 6- to 8-week-old female BALB/c mice (five mice per group) are used in all experiments. The experiment is performed using *Eriodictyon californicum, Eriodictyon sessilifolium*, or *Eriodictyon trichocalyx* plants that have been transformed to express HA1 antigen and wild type (WT) plants.

For oral immunization experiments, groups of 6- to 8-week-old female BALB/c mice (five mice per group) are used. The experiment are performed using Yerba Santa plants that express HA1 antigen and wild type (WT) plants. Each mouse is fed with 2-3 g of fresh leaf tissue over a period of 6-8 h. Control mice receive wild type plant material. Mice are immunized 3 times at 2-week intervals.

For intranasal immunization experiments, groups of 6- to 8-week-old BALB/c mice (five per group) are used. 2 μg of Yerba Santa-derived antigen is administered in 10 μl of saline into both nostrils (5 μl in each). In some groups, plant material is supplemented with 1 μg of CT (cholera toxin) as an adjuvant. Control mice receive wild type plant material. Mice are immunized 3 times at 2-week intervals.

Blood and fecal matter is collected 10 days after each immunization. Protein from fecal pellets will be extracted in PBS (10 vol/wt) supplemented with 1% BSA and protease inhibitors. Mice are killed 10 days after the last immunization and bled by cardiac puncture. Sera and fecal pellets are analyzed for the presence of antigen (HA1) specific antibodies by Western blot analysis and ELISA.

Solid-phase ELISA is carried out as described in Hooper et al. (2001) *J. Immunol.* 167, 3470-3477 MaxiSorp 96-well plates (Nalge Nunc) are coated overnight at 4° C. with the HA1 at a concentration of 1 μg/ml in PBS. Extract are diluted initially 1:10 in PBS and diluted serially 1:2 in the same buffer incubation for 1 hour at 37° C. Antigen-specific antibodies are detected by using the following antibodies: rabbit anti-mouse IgG (total) and anti-mouse IgG1 (both from BD Biosciences Pharmingen), anti-mouse IgG2a, IgG2b, IgG3 and IgA (all from Organon Teknika), and anti-mouse IgE (eBioscience, San Diego) HRP-conjugated (diluted 1:2000 in PBST) for 1 h at 37 C. Between each step, wells are washed four times with PBST. Finally, plates are developed in a solution of OPD peroxidase substrate (Sigma Chemical). Absorbance at 490 nm is determined using a microplate reader.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

In addition, where features or aspects of the invention are described in terms of Markush group or other grouping of alternatives, those skilled in the art will recognized that the invention is also thereby described in terms of any individual member or subgroup of members of the Markush group or other group.

Unless indicated to the contrary, all numerical ranges described herein include all combinations and subcombinations of ranges and specific integers encompassed therein. Such ranges are also within the scope of the described invention.

The disclosures of each patent, patent application and publication cited or described in this document are hereby incorporated herein by reference, in their entirety.

What is claimed:

1. A method for transforming tissue from a plant of the genus *Eriodictyon* tissue comprising the steps of:
- inoculating leaf tissue from an *Eriodictyon* plant with an *Agrobacterium* suspension diluted to about $OD_{600}$ 0.005 to 0.5, the *Agrobacterium* containing at least one genetic component encoding a desired protein capable of being transferred to the leaf tissue and of directing the expression of the desired protein in the plant;
- co-cultivating the leaf tissue with the *Agrobacterium*; wherein the co-cultivating is for no more than two days and/or the *Agrobacterium* suspension is about $OD_{600}$ 0.03 or lower;
- transferring the tissue to recovery media containing an antibiotic for eliminating the *Agrobacterium* and allowing the tissue to recover for at least 7 days; and
- selecting transformed plant tissue.

2. A transgenic plant of the genus *Eriodictyon* produced by regenerating a plant from transformed plant tissue made by the method of claim 1.

3. The transgenic plant of claim 2, wherein the plant is selected from the group consisting of *E. californicum, E. trichocalyx* and *E. sessilifolium.*

4. The transgenic plant of claim 2, which expresses a recombinant protein.

5. The transgenic plant of claim 4 wherein the recombinant protein is selected from the group consisting of antigens, microbicides, antibodies, hormones, enzymes, blood components, interferons, and anticoagulants.

6. The transgenic plant of claim 5 wherein the antigen comprises a viral protein.

7. The transgenic plant of claim 6 wherein the viral protein comprises an avian influenza HA1 antigen.

8. The transgenic plant of claim 5 wherein the microbicide comprises an antiretroviral.

9. The transgenic plant of claim 8 wherein the antiretroviral comprises griffithsin.

10. The method of claim 1 wherein the plant species is selected from the group consisting of *Eriodictyon californicum, Eriodictyon trichocalyx* and *Eriodictyon sessilifolium.*

11. The method of claim 1 wherein the Agrobacterium suspension is diluted to about $OD_{600}$ 0.03.

12. The method of claim 1 wherein the inoculating step is for about 1 to 30 minutes.

13. The method of claim 12 wherein the inoculating step is for about 10 minutes.

14. The method of claim 1 wherein the co-cultivating of the plant tissue with the *Agrobacterium* suspension is for about 1 to 4 days at about 20 to 25° C.

15. The method of claim 14 wherein the co-cultivating of the plant tissue with the *Agrobacterium* suspension is for about 2 days.

16. The method of claim 1 wherein the transferring to recovery media is for about 7 to 20 days.

17. The method of claim 16 wherein the transferring to recovery media is for about 10 days.

18. The method of claim 1 wherein the selecting step comprises transferring the plant tissue to media containing successively higher concentrations of a selective agent.

19. The method of claim 18 wherein the genetic component is capable of conferring kanamycin resistance to the plant tissue and the selective agent is kanamycin.

20. A method for producing a recombinant protein in a transgenic plant of the genus *Eriodictyon* comprising the steps of:
- providing the transgenic plant of claim 2; and
- recovering the protein expressed in the transgenic plant.

21. The method of claim 20 wherein the recovery step further comprises obtaining an extract of the transgenic plant.

22. The method of claim 20 wherein the recovery step further comprises harvesting material from at least a portion of the transgenic plant.

23. The method of claim 22 wherein the at least a portion of the harvested material is edible.

24. The method of claim 20 wherein the plant cell or tissue is transformed using an *Agrobacterium* system.

25. The method of claim 24 wherein the plant cell or tissue is transformed using the method of claim 1.

26. The method of claim 20 wherein the recombinant protein is selected from the group consisting of antigens, microbicides, antibodies, hormones, enzymes, blood components, interferons, and anticoagulants.

27. The method of claim 26 wherein the antigen comprises a viral protein.

28. The method of claim 27 wherein the protein comprises an avian influenza HA1 antigen.

29. The method of claim 26 wherein the microbicide comprises an antiretroviral.

30. The method of claim 29 wherein the antiretroviral comprises griffithsin.

31. A method of delivering a recombinant protein to a subject comprising the steps of;
- providing harvested material from the transgenic plant of claim 2; and
- administering the harvested material to the subject in an amount necessary to deliver an effective amount of the recombinant protein.

32. The method of claim 31 wherein the recombinant protein is an antigen and the harvested material is administered in an amount sufficient to induce an immune response in the subject.

33. The method of claim 31 wherein the harvested material is administered orally.

34. The method of claim 31 wherein the harvested material is administered by contacting a mucosal surface of the subject.

35. The method of claim 34 wherein the recombinant protein is a microbicide and the harvested material is administered in an amount sufficient to provide a prophylactic effect.

36. The method of claim 34 wherein the mucosal surface is selected from the group consisting of nasal, oral, lingual, sub-lingual, buccal, gingival, palatal, vaginal, ocular, auditory, pulmonary tract, urethral, and rectal surfaces.

* * * * *